United States Patent [19]

Santi et al.

[11] Patent Number: 4,950,785

[45] Date of Patent: Aug. 21, 1990

[54] CATALYTIC PROCESS OF SYNTHETIZING ETHYLENE-TETRACARBOXYLIC ESTERS

[75] Inventors: Roberto Santi, Novara; Giuseppe Cometti, Verbania, both of Italy

[73] Assignee: Presidenza del Consilglio dei Ministri Ufficio del Ministro per il coordinamento delle iniziative per la ricerca scientifica e tecnologica, Rome, Italy

[21] Appl. No.: 312,932

[22] Filed: Feb. 21, 1989

[30] Foreign Application Priority Data

Feb. 24, 1988 [IT] Italy ................................ 19507 A/88

[51] Int. Cl.$^5$ ............................................ C07C 67/343
[52] U.S. Cl. .................................... 560/202; 560/190; 562/595; 502/324; 502/326; 502/345
[58] Field of Search ................ 560/202, 190; 502/324, 502/326, 345

[56] References Cited

U.S. PATENT DOCUMENTS 2,426,224  8/1947  Kharasch ...................... 560/202 X
3,956,358  5/1976  Onsager ......................... 560/202 X
4,485,256  11/1984 McKinney ......................... 560/202
4,547,323  10/1985 Carlson ............................ 560/202 X Primary Examiner—Werren B. Lone
Assistant Examiner—Vera C. Clarke
Attorney, Agent, or Firm—Stevens, Davis, Miller & Mosher

[57] ABSTRACT

Process of synthetizing ethylene-tetracarboxylic esters by duplication of malonic compounds of the formula:

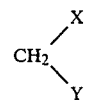

wherein X=COOR, Y=COOR' and R and R' represent an organic group, characterized in that the duplication is an oxidative duplication conducted in the presence of a catalyst consisting of the salt of a transition metal.

9 Claims, No Drawings

CATALYTIC PROCESS OF SYNTHESIZING ETHYLENE-TETRACARBOXYLIC ESTERS

BACKGROUND OF THE INVENTION

The present invention relates to a process of synthetizing ethylene-tetracarboxylic esters of the formula (I) or (II):

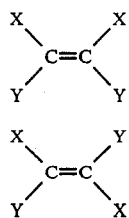

(I)

(II)

starting from malonic compounds of the formula (III):

(III)

wherein X=COOR, Y=COOR' and R and R', the same or different, are organic groups, inert under the synthesis conditions. There are known methods of preparing esters of the formula (I) or (II), where X=Y=-COOR and where R is an alkyl group, starting from malonates and NaOH (25% b.w.) in $CH_2Cl_2$, containing tetrabutylammonium bromide and trichlorobromomethane (see German Patent No. 3,031,348), or by electrolytic duplication of the malonate (see U.S. Pat. Nos. 4,076,601 and 4,659,441); these ethylene-tetracarboxylic esters can be used in detergent formulations or for the production of technopolymers. Furthermore, they can be transformed into pinacol derivatives by catalytic hydroxylation with hydrogen peroxide.

The Applicants have now found that it is possible to obtain the same esters by an alternative simpler, quicker and more advantageous process.

DISCLOSURE OF THE INVENTION

In its widest aspect, the invention relates to a catalytic process of synthetizing ethylene-tetracarboxylic esters of formula (I) or (II):

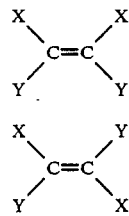

(I)

(II)

by duplication of malonic compounds of formula (III):

(III)

wherein X=COOR, Y=COOR' and R and R', the same or different, represent an organic group inert under the synthesis conditions; the process is characterized in that the duplication is an oxidative duplication, which is carried out by the use of oxygen (or another gas containing oxygen), in the presence of a catalyst consisting of an inorganic (for instance nitrate) or organic salt of a transition metal preferably selected from manganese, cobalt and copper.

Very good results are attained if the work is carried out under anhydrous conditions and in the presence of an organic salt of an alkali metal or of an alkaline earth metal and if the synthesis is performed at 30°–200° C., in a polar solvent, which can solubilize the catalyst. The pressure may be comprised between the atmospheric pressure and 50 bar; the space velocity of the oxidizing gas (oxygen, air, enriched air, poor air or other gases) is at least 2 Normal-liters/h per liter of reacting volume.

The above mentioned groups R and R' of formula (I) and (II) may represent, for instance, alkyl, cycloalkyl, aryl or heterocyclic groups (optionally substituted), containing from 1 to 18 C atoms. As an alkyl group we mean also an arylalkyl group, a (cycloalkyl)alkyl group or an alkyl group substituted with heterocyclic groups, containing O, N or S in the ring; as an aryl group we means also an alkyl-aryl group, a cyclo-alkyl-aryl group or an aryl group substituted with said heterocyclic groups; as a cycloalkyl group we mean also an alkyl-cycloalkyl group, an aryl-cycloalkyl-group or a cyclo-alkyl group substituted with said heterocyclic groups; as a heterocyclic group we mean also an alkyl-, cycloalkyl-, or aryl-heterocyclic group.

Generally, the catalyst is selected from the Mn, Co, Cu salts of carboxylic acids containing from 1 to 22 C atoms; among these salts acetates are preferred; the same catalyst may be used in very little amounts, generally between 0.030 and 0.001 mols of metal (contained in the catalyst) for each mol of the desired tetracarboxylic ester. The polar solvent in which the catalyst dissolves is preferably selected from the aliphatic carboxylic acids containing up to 5 C atoms, in particular acetic acid.

The reaction conditions can be easily maintained under the anhydrous state by adding an anhydride, preferably acetic anhydride. The alkali metal or alkaline earth salt (to be used together with the catalyst) can be advantageously the salt of a carboxylic acid containing from 1 to 22 (and better from 1 to 10) carbon atoms and it can be preferably the sodium salt of acetic acid. Obviously, the reaction temperature (from 30° to 200° C.) is depending on the composition of the reaction mixture and on the desired reaction rate. At the end of the synthesis, the ester of formula (I) is separated, upon distillation of the solvent, by an usual technique, such as for example the extraction by means of organic solvents, followed by precipitation.

It is also advantageous to recover the catalyst from the reaction mixture and to recycle it into the reaction system.

The process of the present invention allows one to obtain the compounds of the formula (I) and (II) with good yields, with a good control of the reaction and therefore by a simple and economic method; therefore, it can be exploited in many an industrial preparation.

Some examples follow to illustrate the invention without limiting the same invention.

EXAMPLE 1

Into a glass reactor provided with agitator, condenser and a control system for the temperature and for the oxygen feed, were loaded:

1 g (0.0037 mols) of $Mn(CH_3COO)_3.2H_2O$
20 g (0.244 mols) of anhydrous $CH_3COONa$
35 g (0.219 mols) of diethyl malonate
33 cm$^3$ of acetic acid
50 cm$^3$ of acetic anhydride Into the mixture 10 liters/h of oxygen were allowed to bubble, while keeping the reaction mixture at 100° C. by means of an external oil bath; after 8 hours, at the end of the reaction, the solvents were removed and a fraction was obtained which contained:

3.0 g (0.018 mols) of diethyl malonate;
1.9 g (0.011 mols) of diethyl ketomalonate;
29.5 g (0.093 mols) of 1,1,2,2-tetraethyl-ethylene-tetracar=boxylate.

Therefore, the tetraethyl-1,1,2,2-ethylenetetracarbo=xylate was obtained with a 85% yield.

EXAMPLE 2

Into the same reactor of example 1 were loaded:
1 g (0.0037 mols) of $Mn(CH_3COO)_3.2H_2O$
20 g (0.244 mols) of anhydrous $CH_3COONa$
60 cm$^3$ of tert. butyl alcohol
40 cm$^3$ of acetic anhydride Into the mixture 10 liters/h of oxygen were allowed to bubble, while keeping the reaction mixture at a lower temperature (80° C.) by means of an external oil bath; after 8 hours, when the reaction was completed, solvents were removed and a fraction containing:

9.2 g (0.057 mols) of diethyl malonate;
2.5 g (0.014 mols) of diethylketomalonate;
22.13 g (0.070 mols) of tetraethyl-1,1,2,2ethylenetetracar=boxylate;

was obtained; the yield was 64%.

What we claim is:

1. Process of synthetizing ethylenetetracarboxylic esters having the formula (I) or (II):

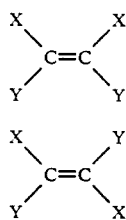

starting from compounds of the formula (III)

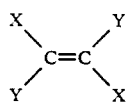

wherein X=COOR, Y=COOR' and R and R', the same or different, represent aklyl groups having from 1 to 18 carbon atoms, inert under the synthesis conditions, characterized by the fact that the duplication is an oxidative duplication, that is performed by use of oxygen or of another oxygen-containing gas, in the presence of a catalyst consisting essentially of the inorganic or organic salt of a transition metal selected from the group consisting of manganese, cobalt and copper.

2. Process according to claim 1, wherein the duplication is performed at 30°-200° C., under anhydrous conditions, maintained by addition of an anhydride, in the presence of an organic salt of an alkali metal or of an alkaline-earth metal.

3. Process according to claim 1 or 2, wherein the duplication is performed at a pressure between atmospheric pressure and 50 bar, in the presence of an organic polar solvent.

4. Process according to claim 1 or 2, wherein the space velocity of the oxidizing gas is equal to or higher than 2 normal-liters/h for each liter of reacting volume.

5. Process according to claim 1 or 2, wherein the catalyst is selected from the class consisting of salts derived from a carboxylic acid containing from 1 to 22 C atoms and from a transition metal selected from the class consisting of Mn, Co and Cu, the amount of catalyst being from 0.030 to 0.001 mols for each mol of tetracarboxylic ester.

6. Process according to claim 1 or 2, characterized in that the tetracarboxylic ester is separated, at the end of the synthesis and upon distillation from the organic solvent, by extraction with an organic solvent followed by precipitation.

7. Process according to claim 1 or 2, wherein the duplication is performed under anhydrous conditions maintained by addition of acetic anhydride, and in the presence of an alkali metal or an alkaline-earth metal salt of a carboxylic acid containing from 1 to 22 carbon atoms.

8. Process according to claim 1 or 2, wherein the duplication is performed in the presence of a polar solvent which is a carboxylic acid containing from 1 to 5 carbon atoms.

9. Process according to claim 1 or 2, wherein the duplication is performed in the presence of acetic acid as polar solvent.